(12) United States Patent
Howell et al.

(10) Patent No.: US 12,017,019 B2
(45) Date of Patent: Jun. 25, 2024

(54) ANTIMICROBIAL DRESSING WITH LINER FOR A MEDICAL DEVICE

(71) Applicant: Bard Access Systems, Inc., Salt Lake City, UT (US)

(72) Inventors: Glade H. Howell, Draper, UT (US); Kelly J. Christian, Draper, UT (US); Mark J. Heninger, South Jordan, UT (US); Jonathan W. Rutledge, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 713 days.

(21) Appl. No.: 16/132,249

(22) Filed: Sep. 14, 2018

(65) Prior Publication Data

US 2019/0083752 A1    Mar. 21, 2019

Related U.S. Application Data

(60) Provisional application No. 62/559,498, filed on Sep. 15, 2017.

(51) Int. Cl.
*A61M 25/02* (2006.01)
*A61L 15/26* (2006.01)
(Continued)

(52) U.S. Cl.
CPC ............ *A61M 25/02* (2013.01); *A61L 15/26* (2013.01); *A61L 15/42* (2013.01); *A61L 15/46* (2013.01);
(Continued)

(58) Field of Classification Search
CPC .......... A61F 13/00063; A61F 13/00085; A61F 13/023; A61F 2013/00182;
(Continued)

(56) References Cited

U.S. PATENT DOCUMENTS 3,428,043 A    2/1969 Shepherd
5,569,207 A *  10/1996 Gisselberg ............ A61M 25/02
                                                    604/175
(Continued)

FOREIGN PATENT DOCUMENTS

DE    102008053335 A1 *  5/2010  ......... A61F 13/0203
WO    WO-9520415 A1 *   8/1995  ............ A61M 25/02
(Continued)

OTHER PUBLICATIONS

Bard Access Systems "Guardiva" 2014.
(Continued)

*Primary Examiner* — Benjamin J Klein
(74) *Attorney, Agent, or Firm* — Rutan & Tucker LLP

(57) ABSTRACT

A full-surround contact antimicrobial dressing is disclosed. The dressing includes a transparent body that covers a skin insertion site through which a catheter assembly passes for disposal within the body of a patient. The transparency of the dressing body enables inspection of the skin insertion site. In one embodiment, therefore, an antimicrobial full-surround contact dressing for use with a medical device inserted into a skin surface of a patient via a skin insertion site is disclosed and comprises a transparent flat body, an antimicrobial adhesive substance disposed on a bottom surface of the body, and a slit defined in the body. The slit is configured to enable the body to be placed fully around a perimeter of the medical device on the skin surface at the skin insertion site such that the bottom surface of the body fully surrounds and contacts the skin insertion site.

22 Claims, 15 Drawing Sheets

(51) Int. Cl.
*A61L 15/42* (2006.01)
*A61L 15/46* (2006.01)
*A61L 15/58* (2006.01)

(52) U.S. Cl.
CPC ......... *A61L 15/58* (2013.01); *A61L 2300/104* (2013.01); *A61L 2300/206* (2013.01); *A61L 2300/404* (2013.01); *A61M 2025/0273* (2013.01); *A61M 2205/0205* (2013.01)

(58) Field of Classification Search
CPC . A61F 2013/00412; A61J 15/26; A61J 15/46; A61J 15/58; A61J 2300/104; A61J 2300/206; A61J 2300/404; A61M 25/02; A61M 2025/0273; A61M 2205/0205
See application file for complete search history.

(56) References Cited

U.S. PATENT DOCUMENTS

| 2002/0198482 | A1 | 12/2002 | Dotta |
| 2005/0075595 | A1 | 4/2005 | Hill |
| 2011/0052664 | A1 | 3/2011 | Tennican et al. |
| 2013/0110025 | A1 | 5/2013 | Donnellan et al. |
| 2013/0131621 | A1 | 5/2013 | Van Holten et al. |
| 2013/0296793 | A1 | 11/2013 | Propp |
| 2015/0320605 | A1 | 11/2015 | Pigg et al. |
| 2016/0015570 | A1 | 1/2016 | Heinecke et al. |

FOREIGN PATENT DOCUMENTS

| WO | WO-2012136954 A1 | * | 10/2012 | ....... A61F 13/00085 |
| WO | 2016038109 A1 | | 3/2016 | |
| WO | WO-2016038109 A1 | * | 3/2016 | ....... A61F 13/00063 |

OTHER PUBLICATIONS

Covalon Technologies Ltd. "IV Clear—Antimicrobial clear Silicone Adhesive Securement Dressing with Chlorhexidine and Silver" 2016.
Dennis G. Maki "A Novel Integrated Chlorhexidine-impregnated Transparent Dressing For Prevention of Vascular Catheter-related Bloodstream Infection: A Prospective Comparative Study in Healthy Volunteers" Society for Healthcare Epidemiology of America (SHEA) Apr. 2008.
Goy et al. "A Review of the Antimicrobial Activity of Chitosan". Polimeros: Ciencia e Tecnologia, vol. 19, No. 3, p. 241-247, 2009.
PCT/US2018/051227 filed Sep. 14, 2019 International Seach Report and Written Opinion dated Feb. 22, 2019.

* cited by examiner

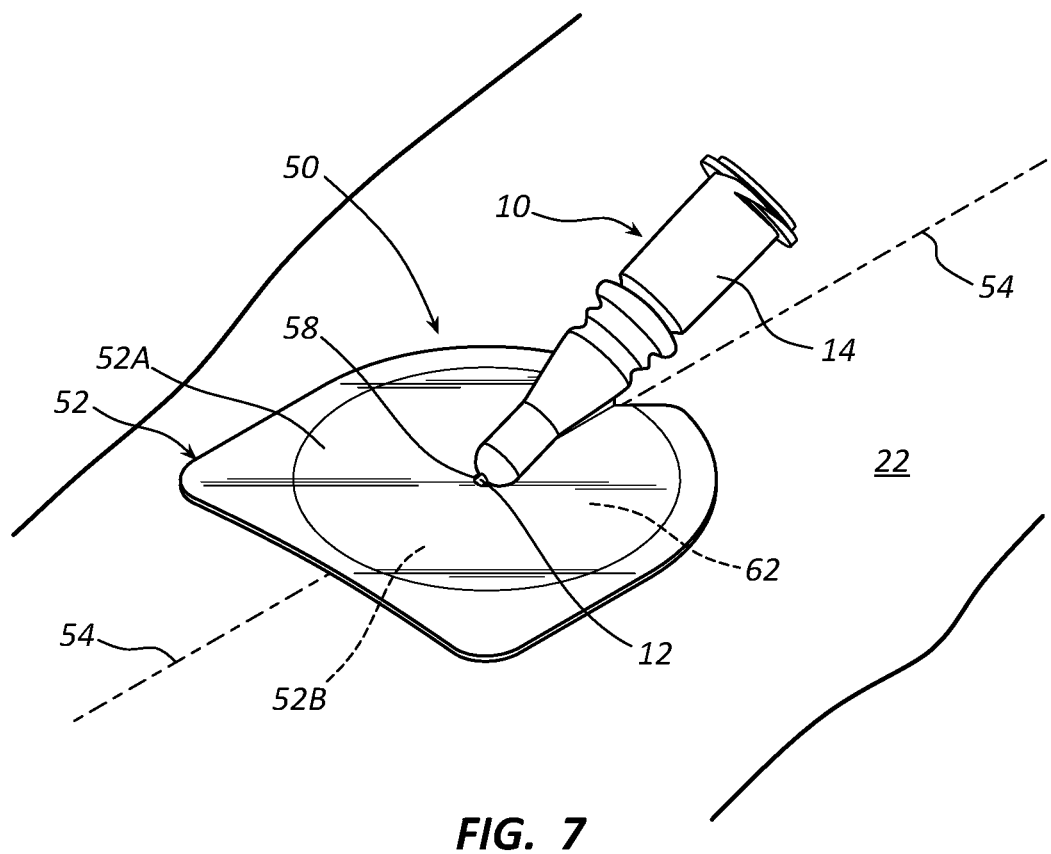
FIG. 7
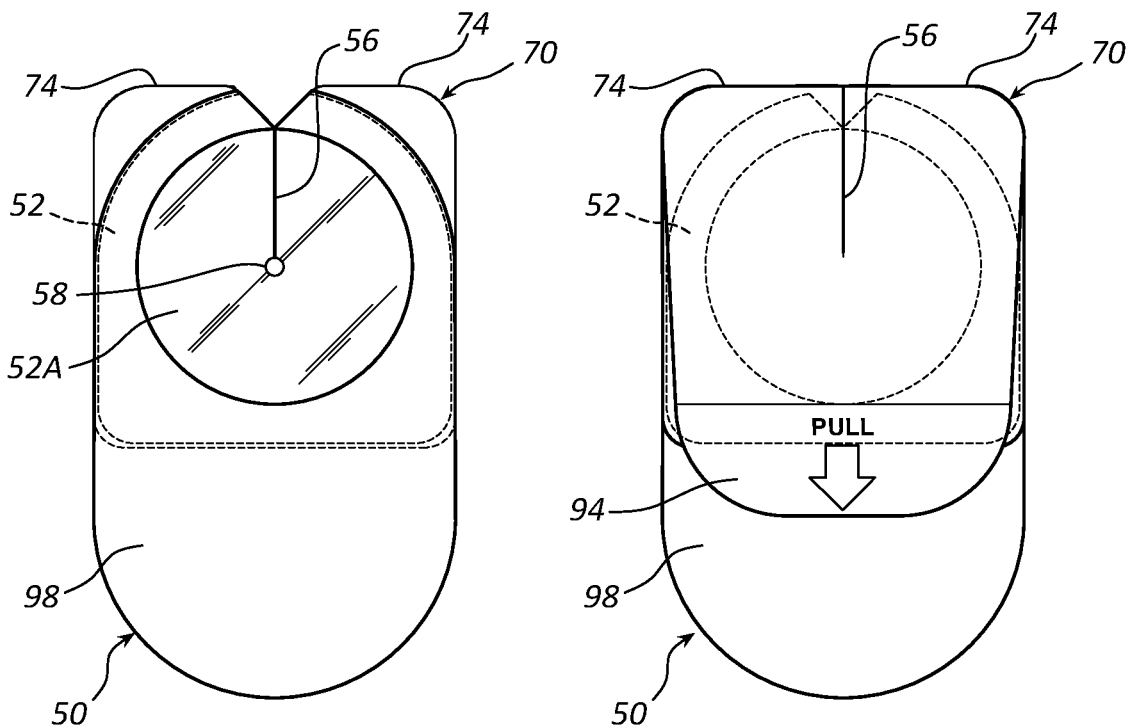
FIG. 8A  FIG. 8B

ANTIMICROBIAL DRESSING WITH LINER FOR A MEDICAL DEVICE

CROSS-REFERENCE TO RELATED APPLICATIONS

This application claims the benefit of U.S. Provisional Patent Application No. 62/559,498, filed Sep. 15, 2017, and entitled "Antimicrobial Dressing with Liner for a Medical Device," which is incorporated herein by reference in its entirety.

BRIEF SUMMARY

Briefly summarized, embodiments of the present invention are directed to a full-surround contact antimicrobial dressing. The dressing includes a transparent body that covers a skin insertion site through which a medical device, such as a catheter assembly, passes for disposal within the body of a patient. The transparence of the dressing body enables inspection of the skin insertion site to determine whether any infection is present.

The transparent body of the dressing further includes a slit, which enables the dressing to fully surround and directly contact all skin surface surround a skin insertion site, thus eliminating "tenting," or partial separation of the dressing from the skin surface. An antimicrobial adhesive substance included on the bottom surface of the dressing body serves to protect the skin insertion site and the skin surface directly surrounding the insertion site from infection.

In one embodiment, therefore, an antimicrobial full-surround contact dressing for use with a medical device inserted into a skin surface of a patient via a skin insertion site is disclosed and comprises a transparent flat body, an antimicrobial adhesive substance disposed on a bottom surface of the body, and a slit defined in the body. The slit is configured to enable the body to be placed fully around a perimeter of the medical device on the skin surface at the skin insertion site such that the bottom surface of the body fully surrounds and contacts the skin insertion site.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 7 is a top view of an antimicrobial dressing positioned about a medical device on a skin surface of a patient;

FIGS. 8A-8C depict various views of the dressing of FIG. 7;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a full-surround contact antimicrobial dressing ("dressing"). The dressing includes a transparent body that covers a skin insertion site through which a medical device, such as a catheter assembly, passes for disposal within the body of a patient. The transparence of the dressing body enables inspection of the skin insertion site to determine whether any infection is present. The transparent body of the dressing further includes a slit, which enables the dressing to fully surround and directly contact all skin surface surround a skin insertion site, thus eliminating "tenting," or partial separation of the dressing from the skin surface. An antimicrobial substance included on the bottom surface of the dressing body serves to protect the skin insertion site and all skin surface directly surrounding the insertion site from infection.

Figure 1:
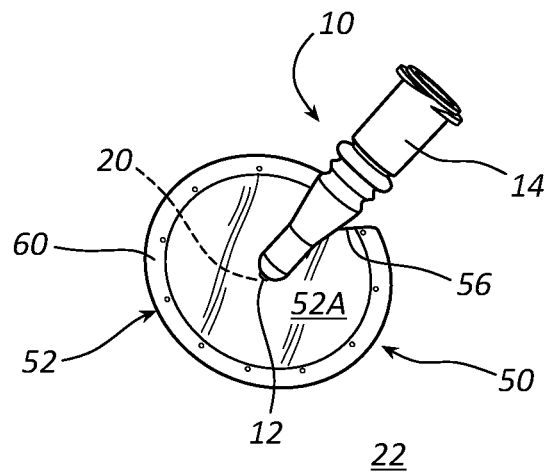
FIG. 1 is a top view of an antimicrobial dressing positioned about a medical device on a skin surface of a patient.

Reference is first made to FIG. 1, which depicts various details of a full-surround contact antimicrobial dressing ("dressing"), generally designated at 50, according to one embodiment. As shown, after deployment the dressing 50 is disposed about a catheter assembly ("catheter") 10, including a catheter tube 12 and a hub 14 attached to a proximal end of the catheter tube. The catheter tube 12 extends through a skin surface 22 into a body of a patient via a skin insertion site 20. Note that, though the discussion herein focuses on use of the dressing with a peripheral IV-type of catheter, other types of catheters and medical devices can benefit from use of the dressing. Examples of such catheters and medical devices include PICCs, central catheters, dialysis catheters, midline catheters, urinary catheters, arterial catheters, femoral lines, feeding tubes, etc.

Figure 2A:
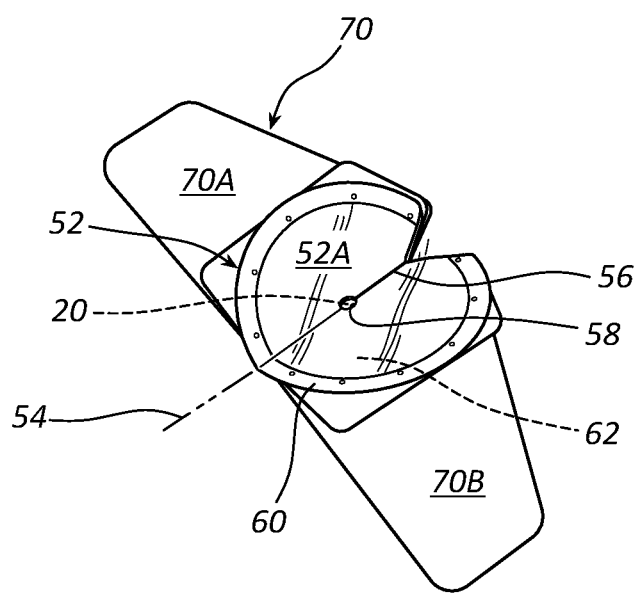
FIGS. 2A-2C depict various views of the dressing of FIG. 1.
Figure 2B:
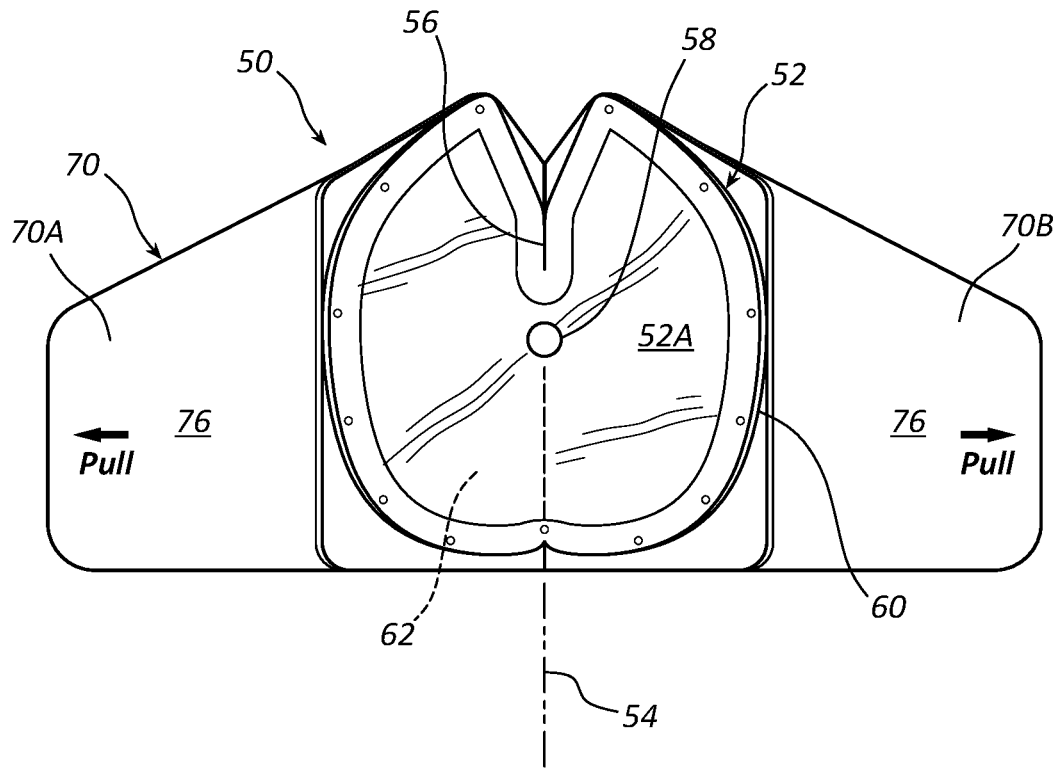
Figure 2C:
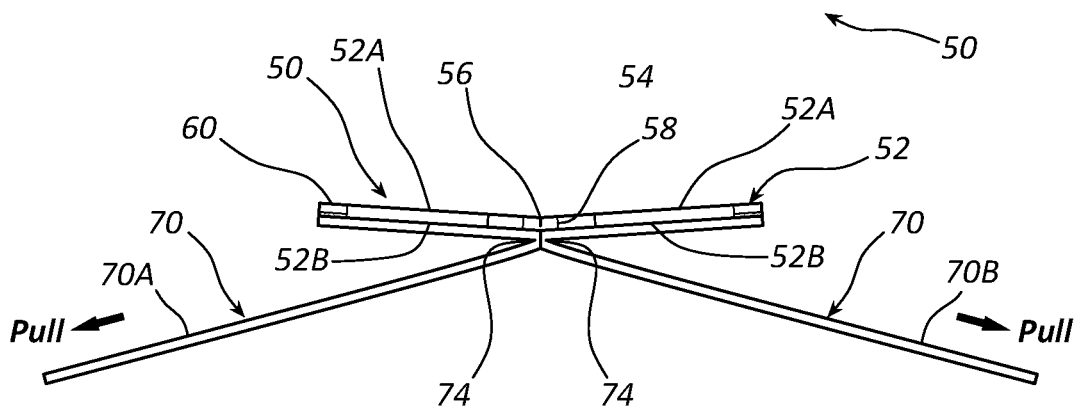

Along with FIG. 1, reference is further made to FIGS. 2A-2C in describing various details of the dressing 50. In particular, the dressing 50 includes a flat body 52, shown here as disk-like in shape, though it is appreciated that the dressing can assume many different shapes, including square, triangular, trapezoidal, rectangular, etc. The body 52 defines an upward-facing top surface 52A and a bottom surface 52B, which is disposed against the skin surface 22. The body 52 is transparent in the present embodiment, so as to enable visual observation of the skin surface 22 disposed below the dressing 50. In the present embodiment, the body 52 is composed of a polyurethane film substrate, though it is appreciated that other suitable transparent materials can be employed for the body. In one embodiment, desirable characteristics for the body material include sufficient breathability so as to not trap moisture underneath the dressing, visual transparency, and suitability for a medical application against the skin. Note that in the present embodiment, the transparent body 52 of FIG. 1 is a film of about 1 mil in thickness, though other structures and thicknesses are possible. Also, note that the body 52 can include a color hue while still remaining sufficiently transparent to observe the skin insertion site below the dressing 50.

A slit 56 is defined along a mid-line 54 of the body 52, extending from a central hole 58 to an outer perimeter of the body. Note that the slit 56 can be disposed in other locations on the body 52. A reinforcement component is also included on the body 52. In the present embodiment, the reinforcement component includes a reinforcement ring 60 secured to an outer perimeter of the body 52 and extending inward along a portion of the slit 56. In the present embodiment, the reinforcement ring 60 is composed of an acrylic material so as to be semi-rigid and provide a suitable amount of rigidity to the body 52, though it is appreciated that other materials can be used, including other thermoplastics, paper, etc. Also, the reinforcement component can include one of various shapes and configurations in addition to those discussed herein.

An adhesive 62 is included on the bottom surface 52B of the body 52, which is configured to adhere the dressing 50 to the skin surface 22 (FIG. 1). The adhesive 62 in the present embodiment is a substantially transparent silicone-based adhesive, though other suitable substantially transparent adhesives can be employed including acrylic adhesives, hydrocollidal substances, etc. The adhesive 62 includes an antimicrobial substance configured to prevent microbial colonization at and proximate to the skin insertion site 20. In the present embodiment, the antimicrobial substance includes a combination of chlorhexadine gluconate ("CHG") and silver. In the present embodiment the adhesive 62 includes an antimicrobial silicone adhesive sold under the mark COVACLEAR™ by Covalon Technologies, Mississauga, Ontario, Canada. It is appreciated that other antimicrobial substances can be employed, including iodine, alcohol, etc. Also, note that the adhesive and antimicrobial substance can include a color hue while still remaining sufficiently transparent to observe the skin insertion site below the dressing 50.

A removable release liner 70 is included with the dressing 50 before deployment on to the skin surface 22 so as to protect the adhesive 62 from contact with unintended surfaces prior to dressing deployment. As such, the release liner 70 includes a coated paper or other suitable product that is removably attached to the adhesive 62 on the bottom surface 52B of the body 52. In the illustrated embodiment, the release liner 70 includes first and second liners 70A, 70B that meet along the midline 54 and cover the bottom surface 52B of the body 52. As seen in FIGS. 2C and 3B, the liners 70A and 70B each include a notch 72 and a fold 74, and the fold of each liner meets one another at the midline 54. Outer portions of each release liner 70A and 70B define pull-tab portions 76 suitable for grasping by a user, as will be explained.

Figure 3A:
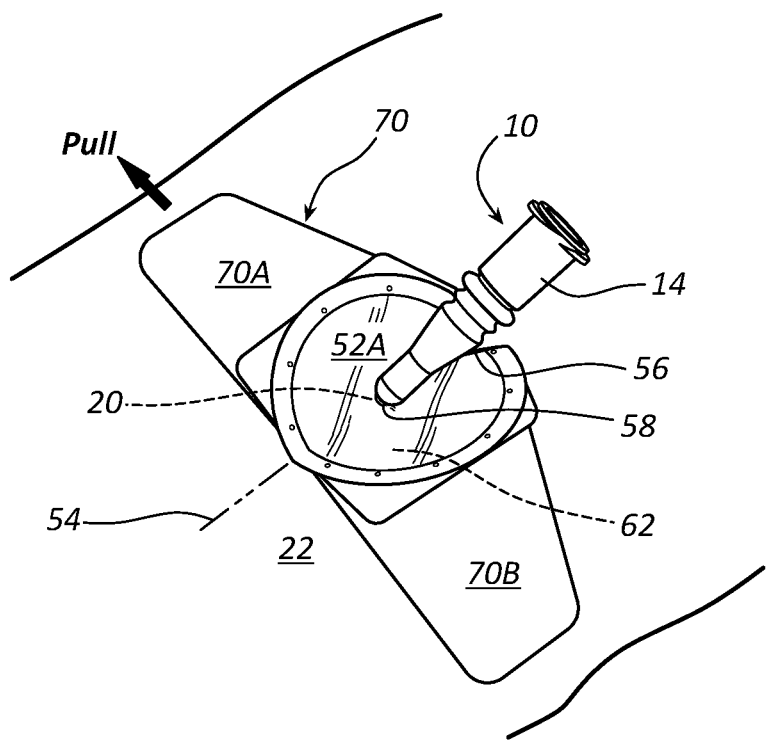
FIGS. 3A-3D depict various views of a procedure for applying the dressing of FIG. 1.
Figure 3B:
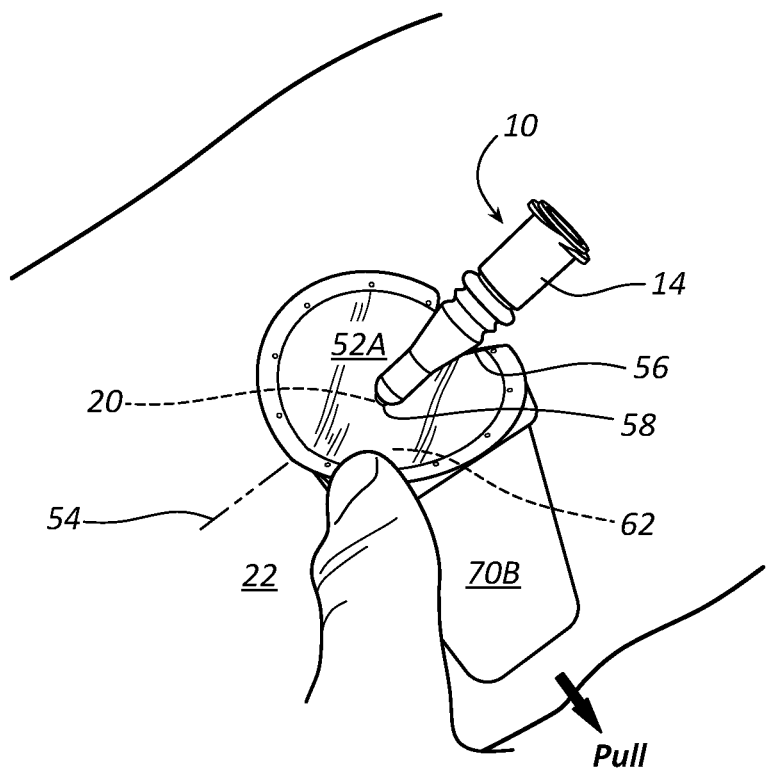

FIGS. 3A-3D show the manner of deployment of the dressing 50 of FIGS. 1-2C on the skin surface 22 to fully surround and contact the circumference of the skin insertion site 20, through which the catheter tube 12 of the catheter 10 passes, on the skin surface 22 of the patient. In FIG. 3A, the dressing 50 is fit by a user about the catheter 10 by receiving a proximal portion of the catheter tube 12 proximate the skin insertion site 20 into the slit 56 until it seats in the central hole 58 and the dressing rests on the skin surface 22.

Next, one of the release liners 70, such as the release liner 70A, is removed by the user by securing the dressing body 52 with one finger and removing the release liner with another finger grasping and pulling the corresponding pull-tab portion 76 of the release liner 70A, resulting in the configuration shown in FIG. 3B.

Figure 3C:
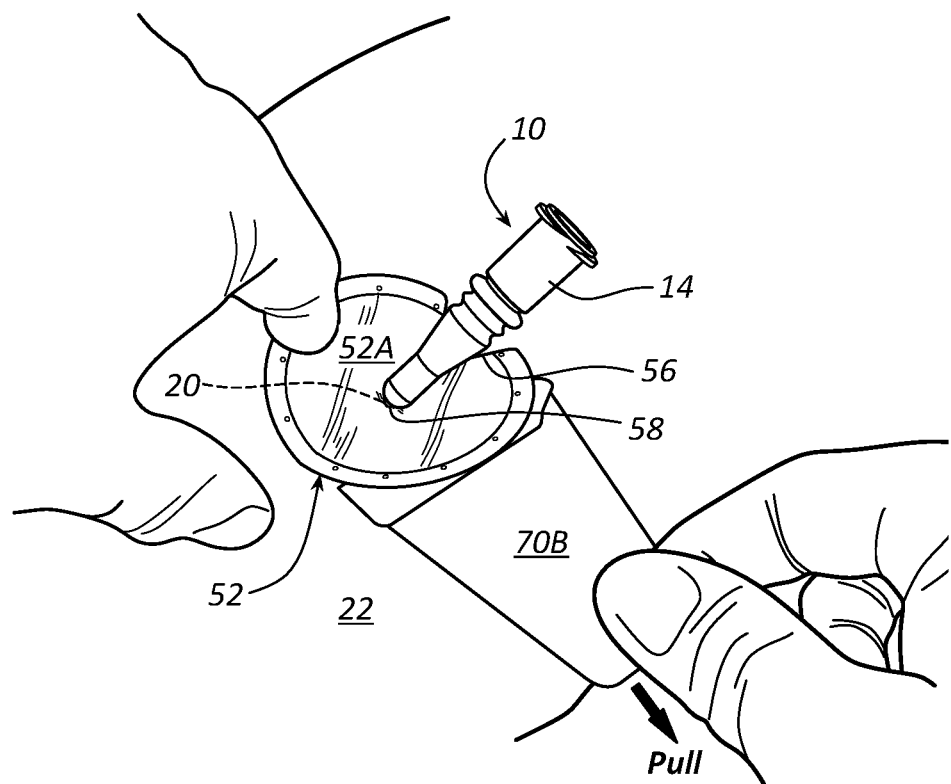
Figure 3D:
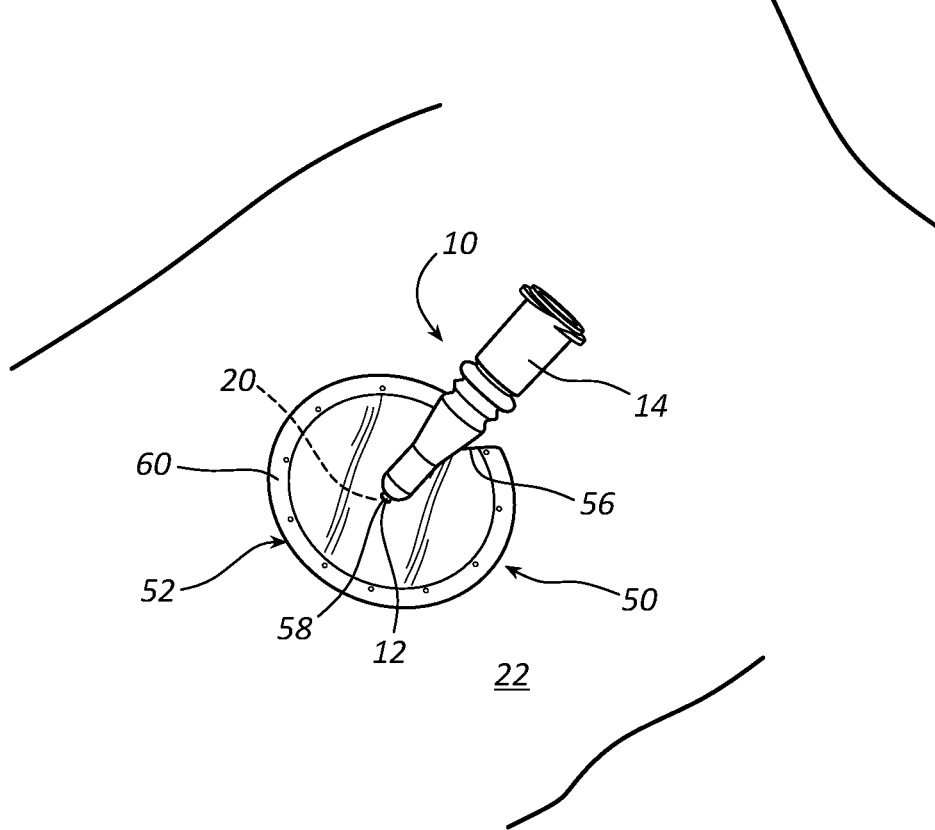

The remaining release liner 70, such as the release liner 70B, is removed by the user by securing the dressing body 52 with one finger and removing the release liner with another finger grasping and pulling the corresponding pull-tab portion 76 of the release liner 70B, as shown in FIG. 3C and resulting in the configuration shown in FIG. 3D. The dressing body 52 can be pressed down against the skin and around the catheter tube 12 to ensure the adhesive 62 on the bottom surface 52B secures the dressing 50 in place on the skin surface 22.

Note that the slit 56 enables the body 52 to fully surround and contact the skin insertion site 20, through which the catheter tube 12 passes, about the perimeter of the catheter tube (or other medical device passing through the skin). This leaves no portion of the region immediately surrounding the skin insertion site 20 uncovered. The presence of antimicrobial substance with the adhesive 62 on the bottom surface 52B of the body 52 desirably assists in preventing the colonization of microbes at the skin insertion site 20. Note that the substrate forming the body 52 is sufficiently breathable in the embodiments described herein so as enable moisture from the skin surface 22 to pass through the body, which in turn can assist in dispersing the antimicrobial substance about the skin insertion site and immediately adjacent areas of the skin surface 22.

Further, because the body 52 is transparent, a clinician can readily observe the skin insertion site 20 through the transparent dressing body 52 to determine whether any infection is present and to observe the insertion site generally.

The configuration shown in FIG. 3D (along with the other embodiments described herein) is in contrast to other dressings, which may not fully surround the skin insertion site or may be disposed atop the catheter 10, resulting in "tenting" of the dressing over the catheter, which leaves portions of the region immediately surrounding the skin insertion site to be uncontacted by the dressing, thus preventing antimicrobial substance to be in contact therewith. The configuration shown in FIG. 3D (along with the other embodiments described herein) is in further contrast to other dressings, which do not include a transparent body to enable direct observation of the skin insertion site.

Figure 4:
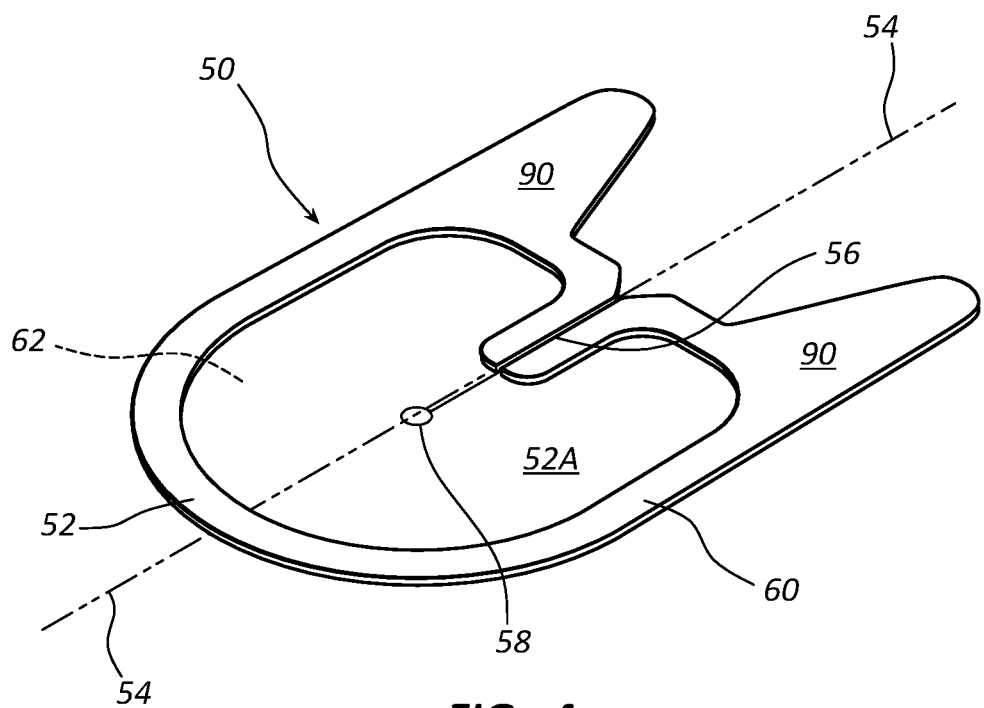
FIG. 4 is a top view of an antimicrobial dressing according to one embodiment.
Figure 5A:
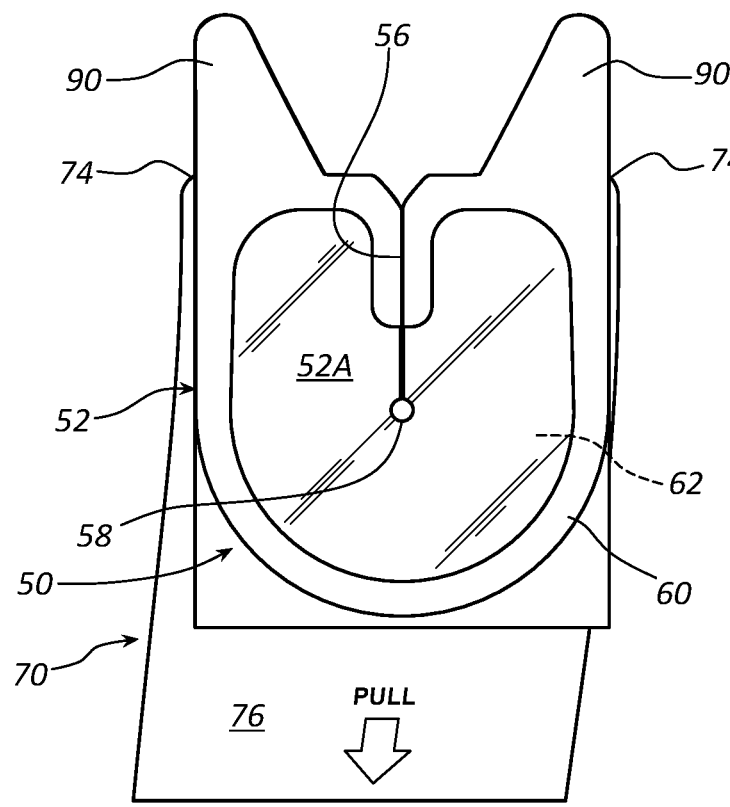
FIGS. 5A and 5B depict various views of the dressing of FIG. 4.
Figure 5B:
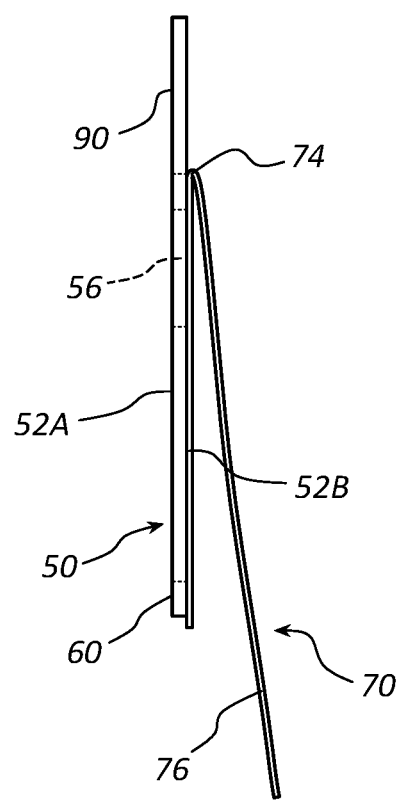

Reference is now made to FIG. 4, which depicts various details of the dressing 50 according to another embodiment, wherein the reinforcement ring 60 in the present embodiment includes a foam structure adhered to the top surface 52A of the body 52. The reinforcement ring 60 further defines two securement tabs 90 configured to keep the dressing 50 in place during deployment on the skin surface 22 of the patient, as will be described. As seen in FIGS. 5A and 5B, the release liner 70 of the illustrated dressing 50 is a singular liner releasably covering the antimicrobial adhesive 62 disposed on the bottom surface 52B of the body 52. The release liner 70 is rectangle-shaped in the present embodiment and includes the fold 74 so as to double back on itself proximate to the securement tabs 90, thus not extending under the securement tabs. The release liner includes the pull-tab portion 76 extending out from under the body 52, best seen in FIG. 5A. Note that the slit 56 and central hole 58 are defined both through the body 52 and the release liner 70. Note also that, in this and other embodiments, one or more securement tabs can be placed in various locations about the perimeter of the dressing 50.

Figure 6A:
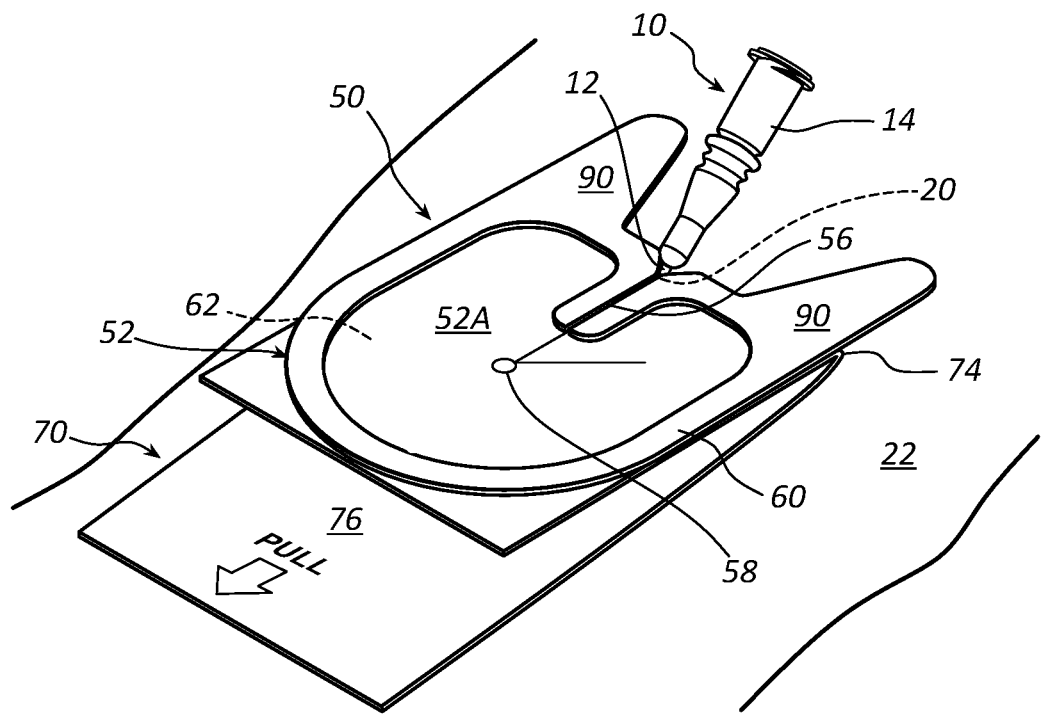
FIGS. 6A-6F depict various views of a procedure for applying the dressing of FIG. 4.
Figure 6B:
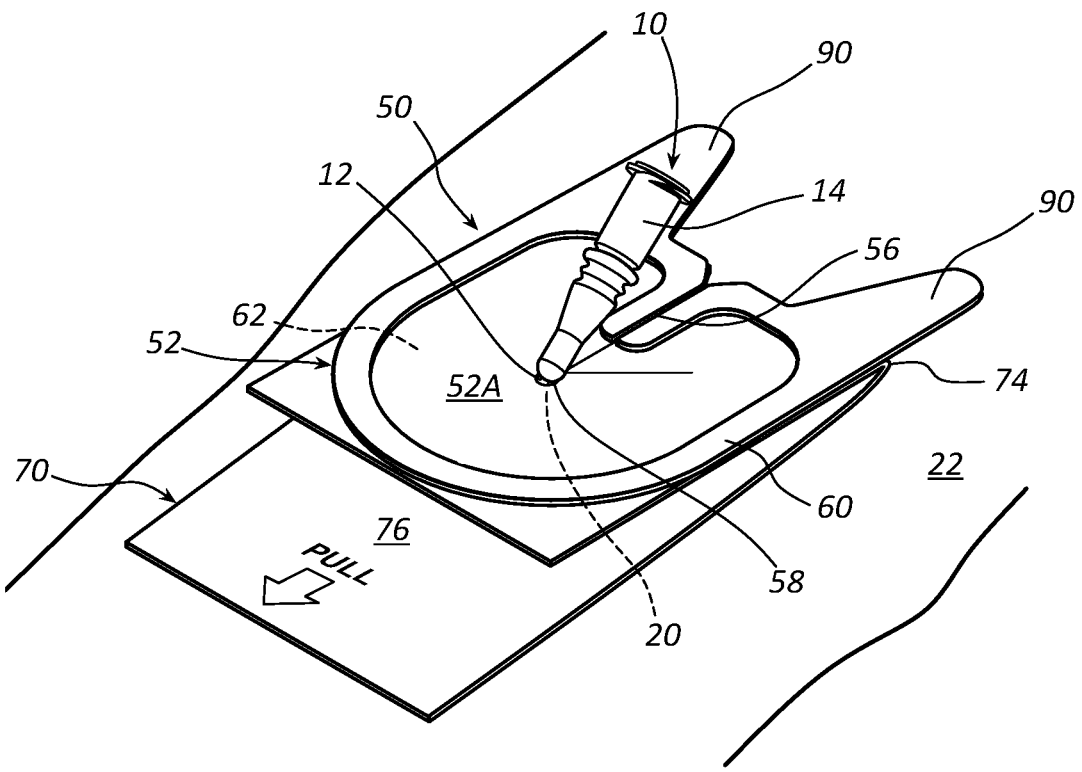

FIGS. 6A-6F show the manner of deployment of the dressing 50 of FIGS. 4-5B on the skin surface 22 to fully surround and contact the circumference of the skin insertion site 20, through which the catheter tube 12 of the catheter 10 passes, on the skin surface 22 of the patient. In FIGS. 6A and 6B, the dressing 50 is fit by a user about the catheter 10 by receiving a proximal portion of the catheter tube 12 proximate the skin insertion site 20 into the slit 56 until it seats in the central hole 58 and the dressing rests on the skin surface 22. Note that the underside of the securement tabs 90 includes no adhesive so as to enable the dressing 50 to be slid on the skin surface to engage the catheter without the securement tabs adhering to the skin and possible folding back on themselves. In one embodiment, note that the underside of the securement tabs 90 includes a coated slick surface.

Figure 6C:
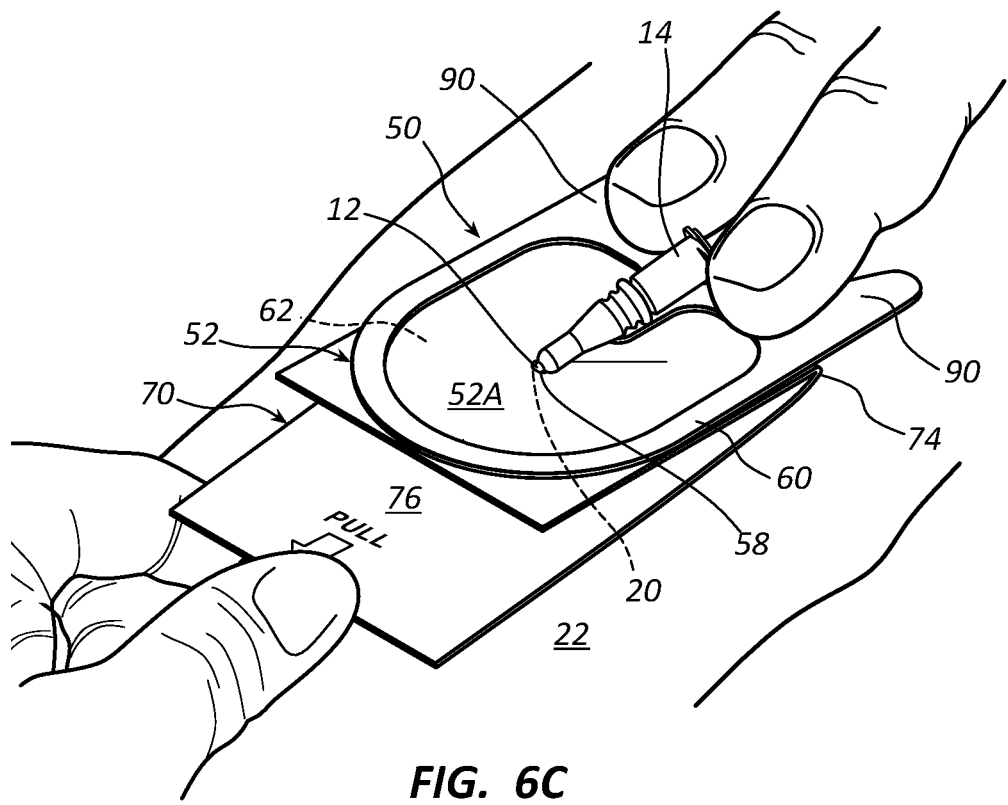
Figure 6D:
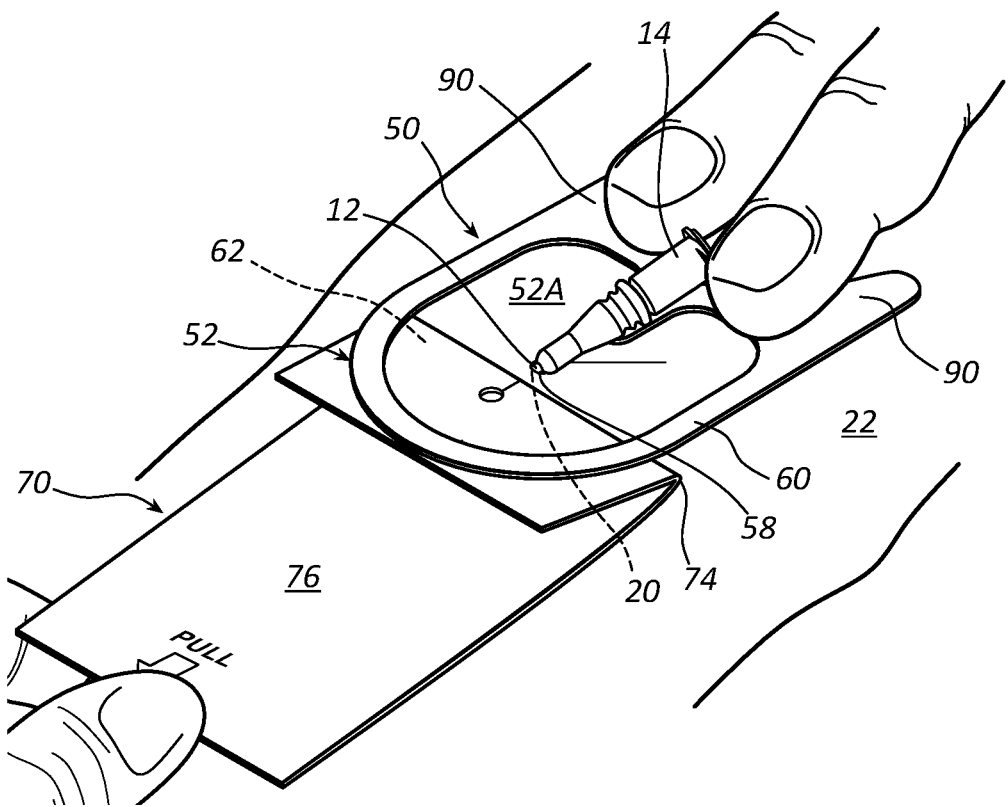
Figure 6E:
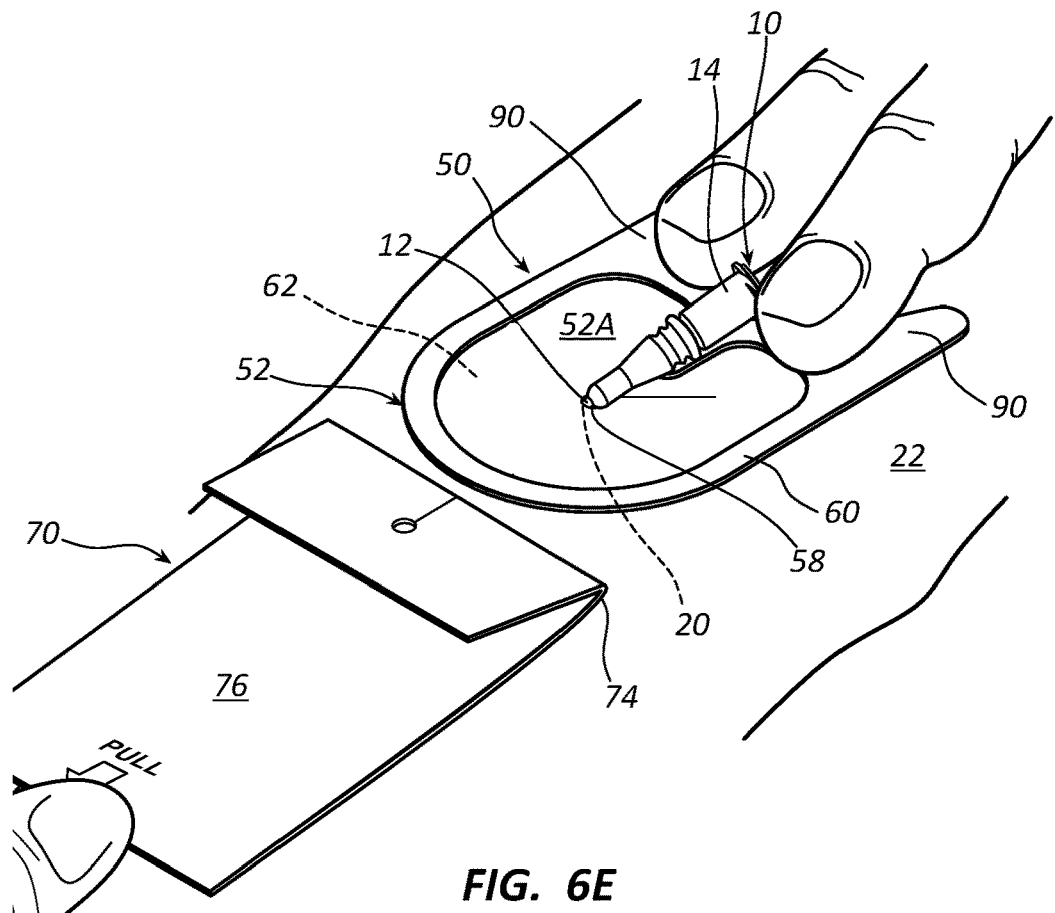
Figure 6F:
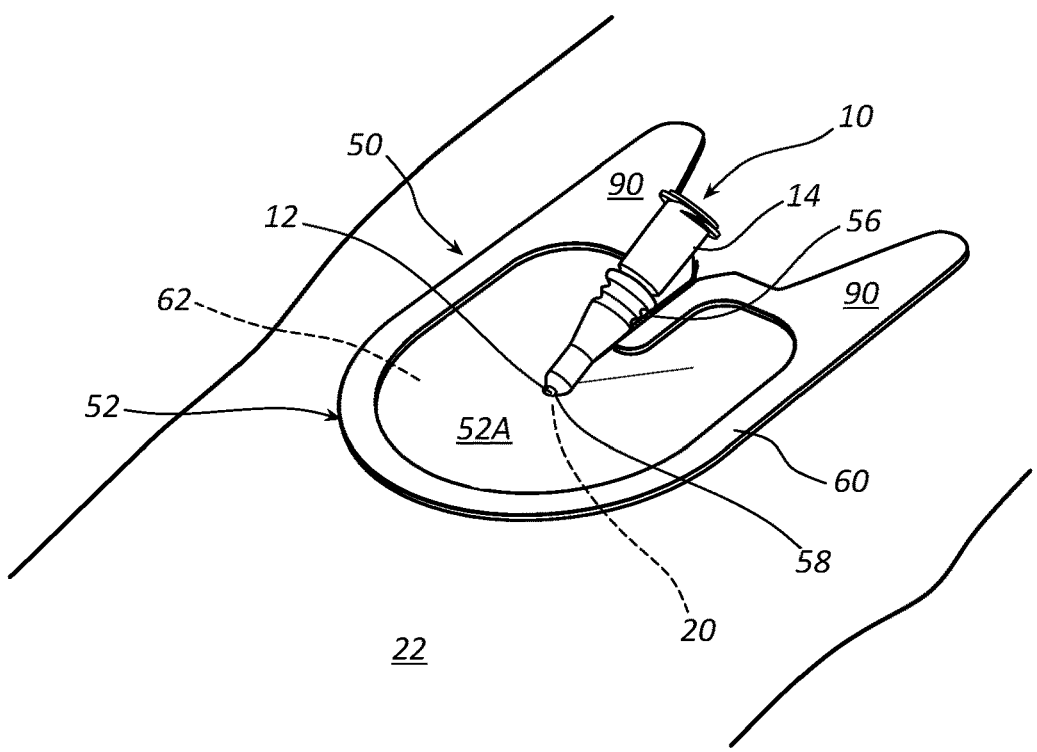

Next, the user applies downward pressure to the securement tabs 90 with two fingers while grasping the pull-tab portion 76 and pulling the release liner 70 away from the dressing body 52 with other fingers as shown in FIG. 6C-6D, resulting in the configuration shown in FIG. 6E. The finger pressure applied to the securement tabs 90 maintains the dressing body 52 in place while the release liner 70 is removed.

The dressing body 52 can be pressed down against the skin and around the catheter tube 12 to ensure the antimicrobial adhesive 62 on the bottom surface 52B secures the transparent dressing 50 in place on the skin surface 22. Note again that the slit 56 enables the body 52 to fully surround and contact the skin insertion site 20, through which the catheter tube 12 passes, about the circumference of the skin insertion site. This leaves no portion of the region immediately surrounding the skin insertion site 20 uncovered.

Figure 8C:
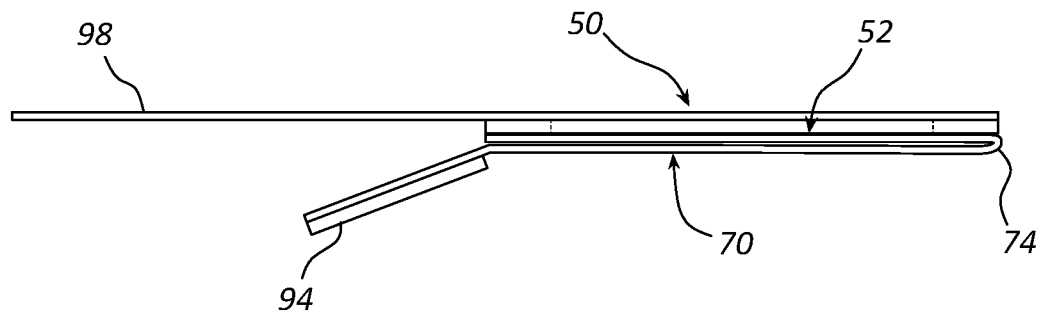

Reference is now made to FIG. 7, which depicts various details of the dressing 50 according to another embodiment. In particular, FIG. 7 shows the dressing 50 deployed about the catheter on the skin surface 22 of the patient. FIGS. 8A-8C show that the dressing 50 prior to deployment includes a reinforcement frame 98 removably adhered to the top surface 52A of the body 52. The reinforcement frame 98 includes coated paper in the illustrated embodiment and is shaped to provide an opening to the top surface 52A of the body 52 about the central hole 58 and to provide a finger grip portion for deployment of the dressing 50, as will be seen.

As seen in FIGS. 8A-8C, the release liner 70 of the illustrated dressing 50 is a singular liner releasably covering the antimicrobial adhesive 62 disposed on the bottom surface 52B of the body 52. The release liner 70 is rectangle-shaped in the present embodiment and includes the fold 74 so as to double back on itself proximate the end point of the slit 56 (which slit extends through the body 52 and the release liner 70). In the present embodiment, the release liner 70 is a polyethylene film treated with fluorosilicone or other suitable non-stick surface so as to not stick to the adhesive 62 disposed on the bottom surface 52B of the body 52. The release liner 70 includes a grasp tab 94 disposed on a terminal free end of the release liner, as best seen in FIGS. 8B and 8C, configured to assist in the removal of the release liner 70, as is described below.

Figure 9A:
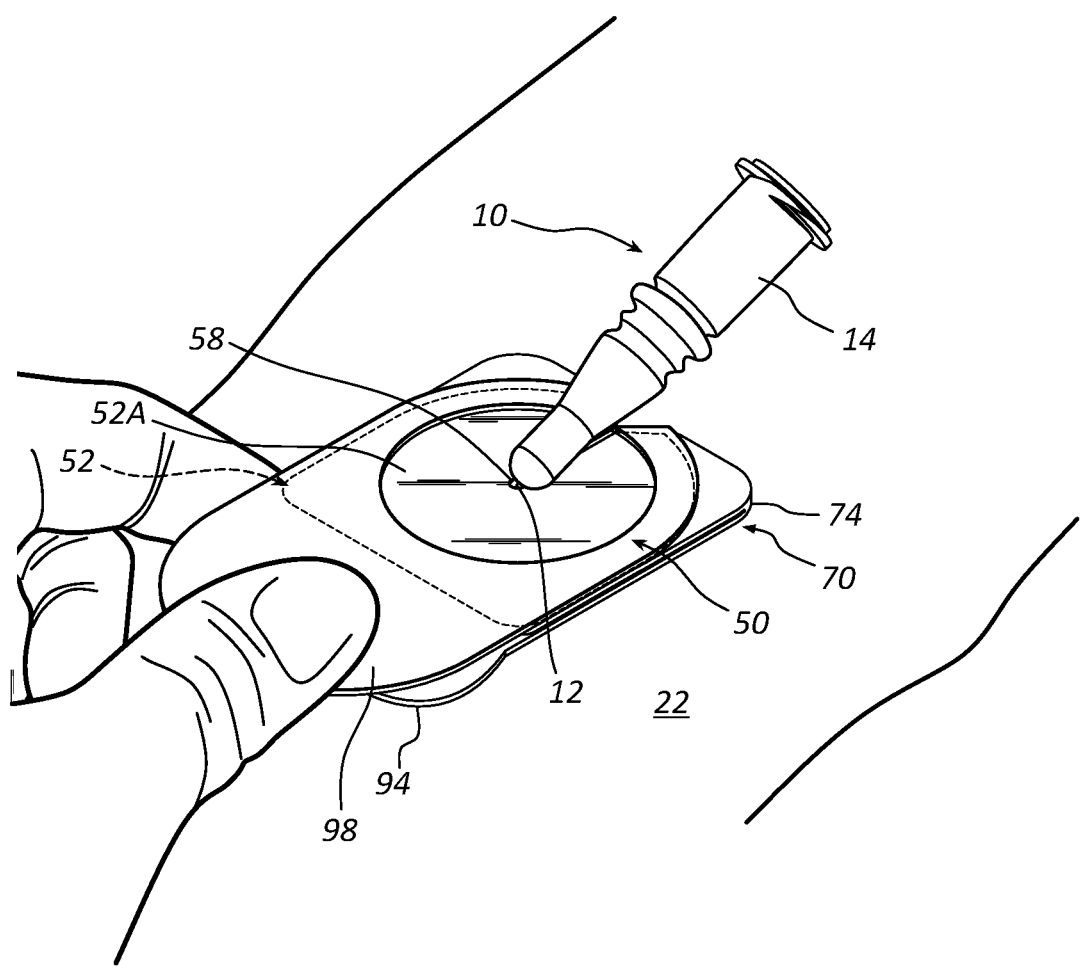
FIGS. 9A-9G depict various views of a procedure for applying the dressing of FIG. 7.

FIGS. 9A-9G show the manner of deployment of the dressing 50 of FIGS. 7-8C on the skin surface 22 to fully surround and contact the circumference of the skin insertion site 20, through which the catheter tube 12 of the catheter 10 passes, on the skin surface 22 of the patient. In FIG. 9A, the dressing 50 is fit by a user about the catheter 10 by receiving a proximal portion of the catheter tube 12 proximate the skin insertion site 20 into the slit 56 until it seats in the central hole 58 and the dressing rests on the skin surface 22.

Figure 9B:
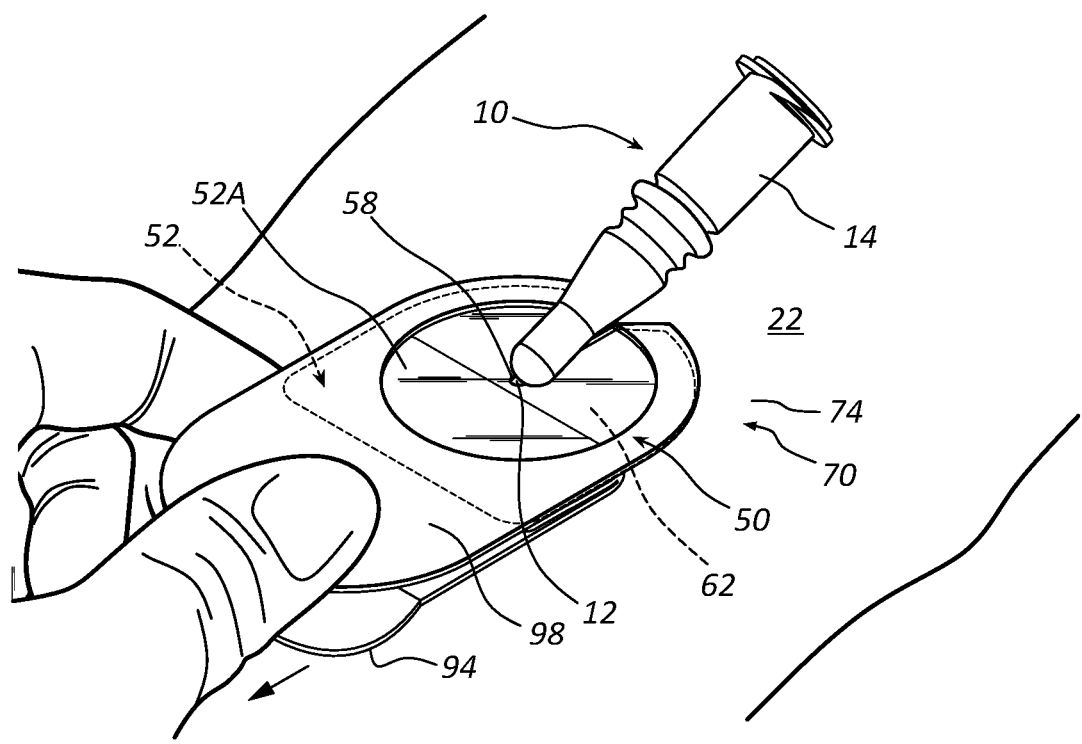
Figure 9C:
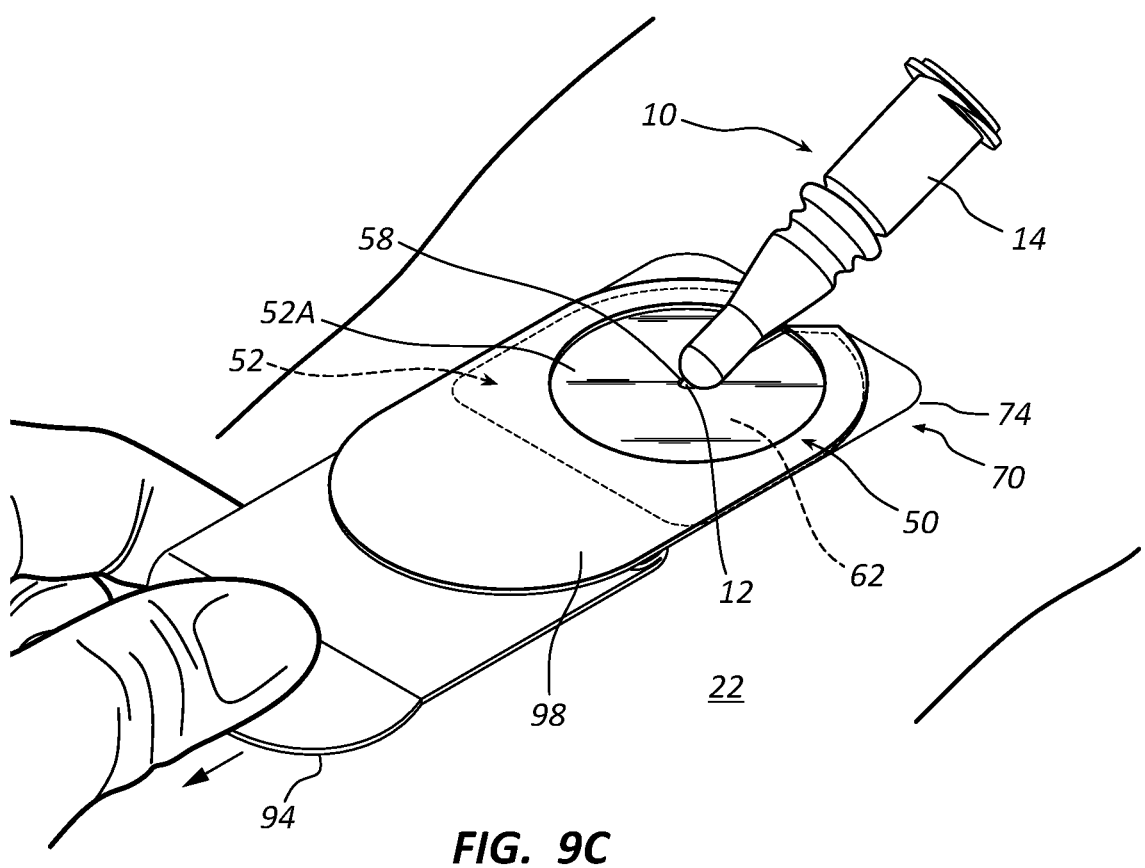
Figure 9D:
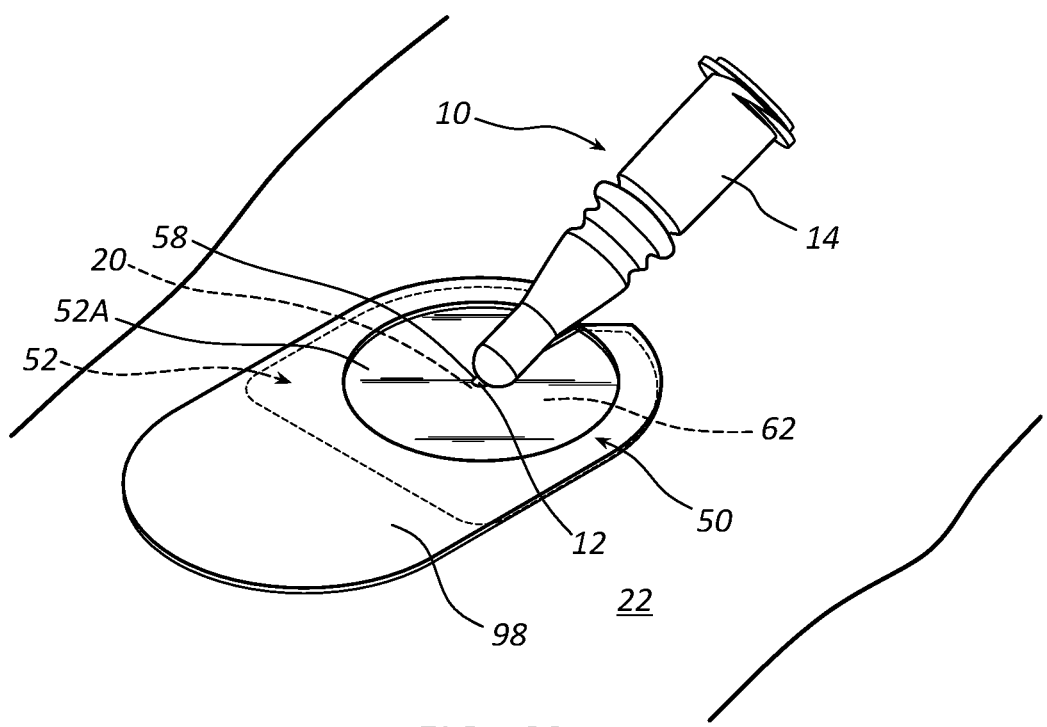

Next, the user grasps the extended portion of the reinforcement frame 98 and the grasp tab 94 (of the release liner 70) between the user's thumb and forefinger/middle finger. While thus grasping the dressing 50, the user slides the release liner 70 off of and away from the bottom surface 52B of the body 52 as shown in FIGS. 9B and 9C, resulting in the configuration shown in FIG. 9D. The relative movement of the forefinger/middle finger with respect to the thumb (which is placed on top of the reinforcement frame 98) helps to maintain the dressing body 52 in place while the release liner 70 is removed.

The dressing body 52 can be pressed down against the skin and around the catheter tube 12 to ensure the antimicrobial adhesive 62 on the bottom surface 52B secures the transparent dressing 50 in place on the skin surface 22. Note again that the slit 56 enables the body 52 to fully surround and contact the skin insertion site 20, through which the catheter tube 12 passes, about the circumference of the skin insertion site. This leaves no portion of the region immediately surrounding the skin insertion site 20 uncovered.

Figure 9E:
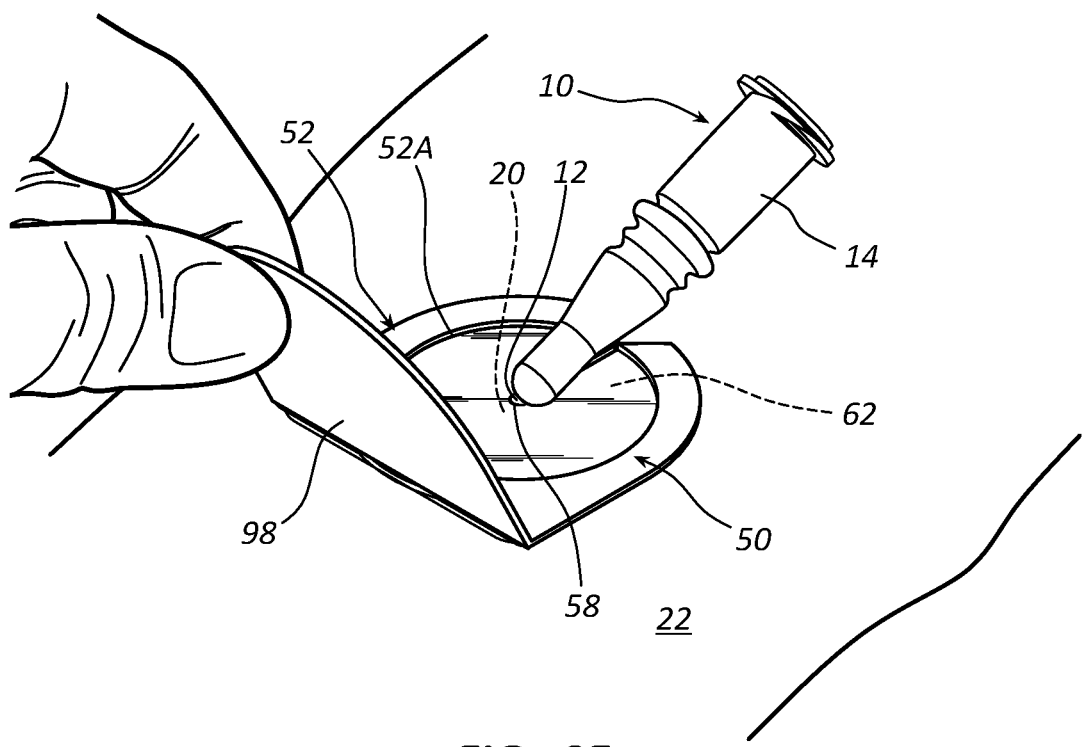
Figure 9F:
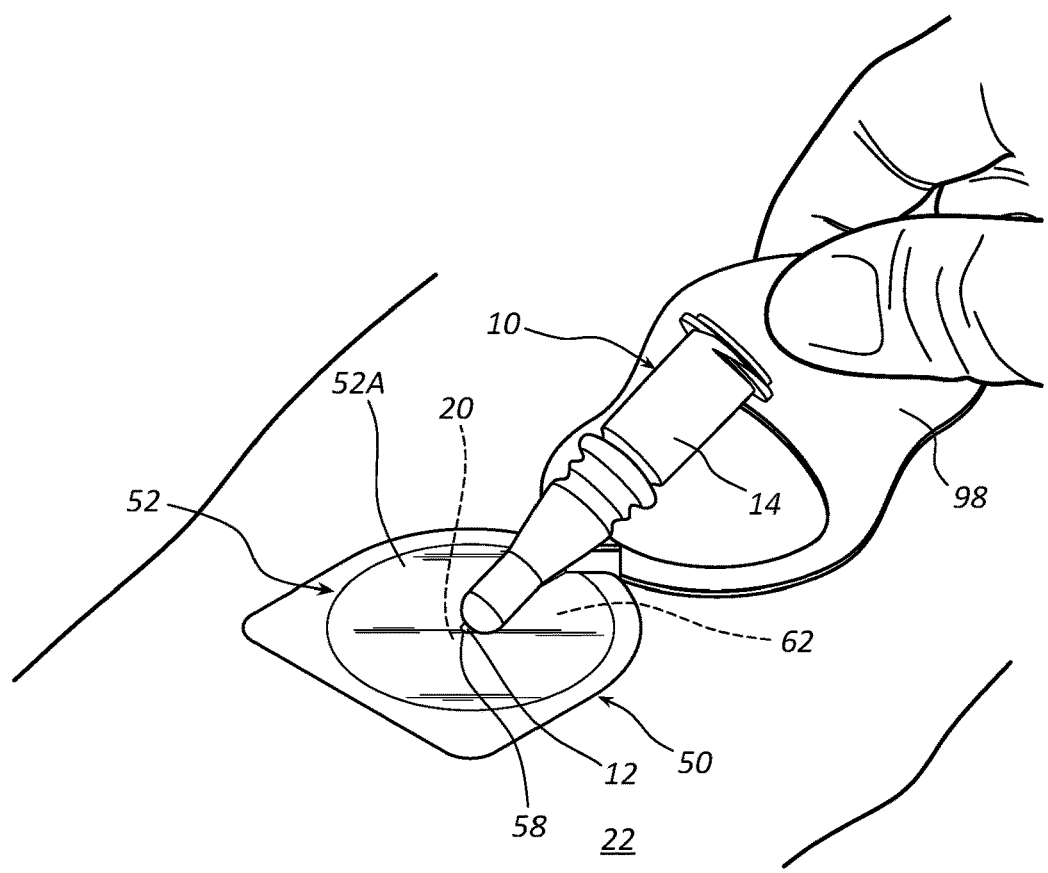
Figure 9G:
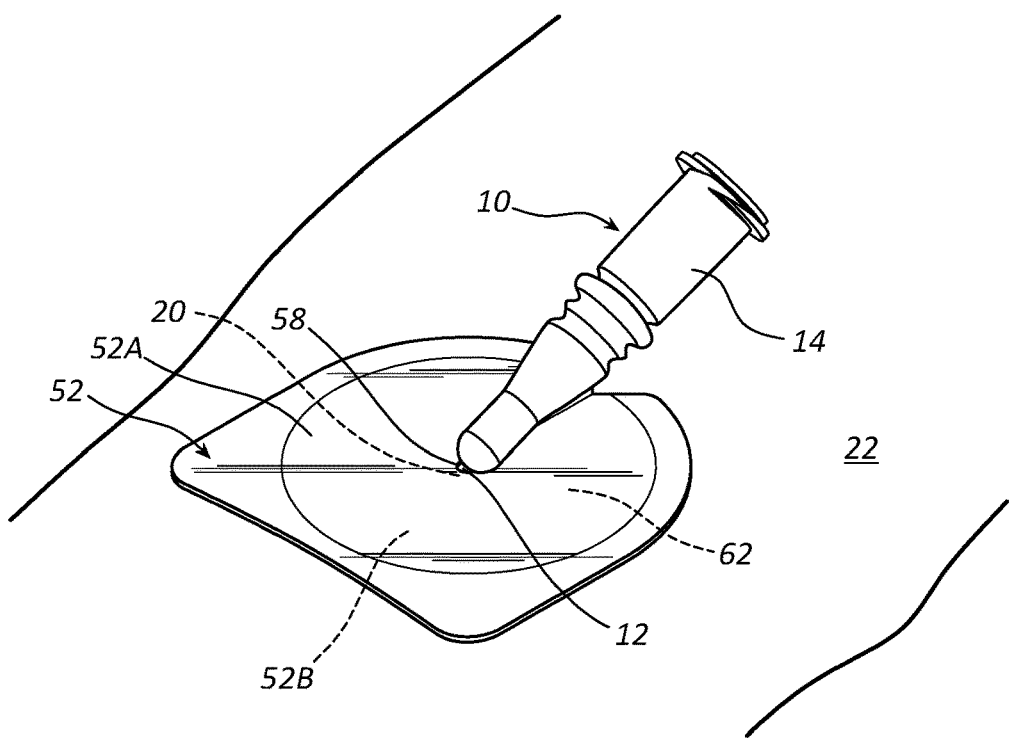

As shown in FIGS. 9E and 9F, the reinforcement frame 98 can be removed from the dressing body 52 by lifting and peeling it away from the body. The dressing body 52 is now deployed in place on the skin surface 22, as shown in FIG. 9G.

Figure 10:
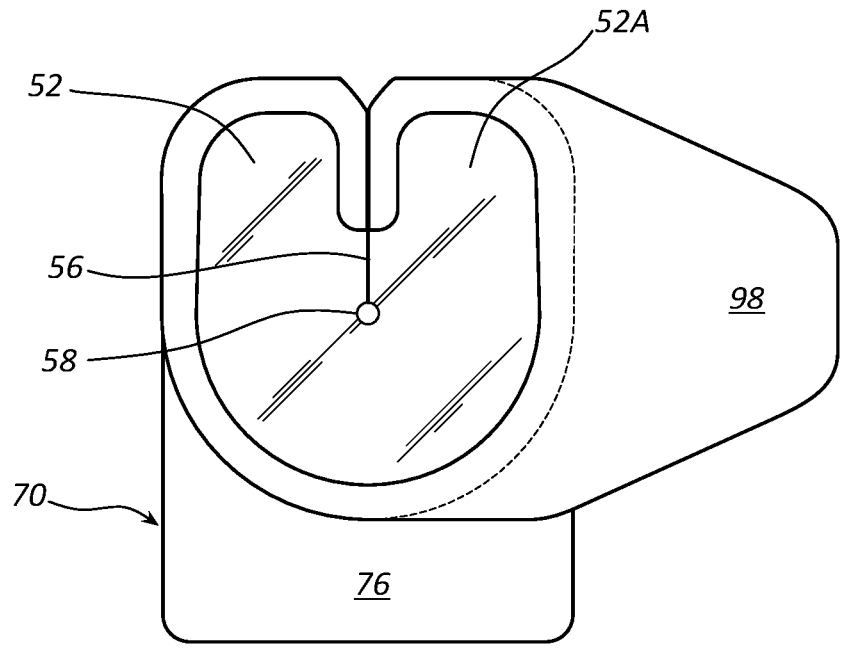
FIG. 10 is a top view of an antimicrobial dressing.
Figure 11:
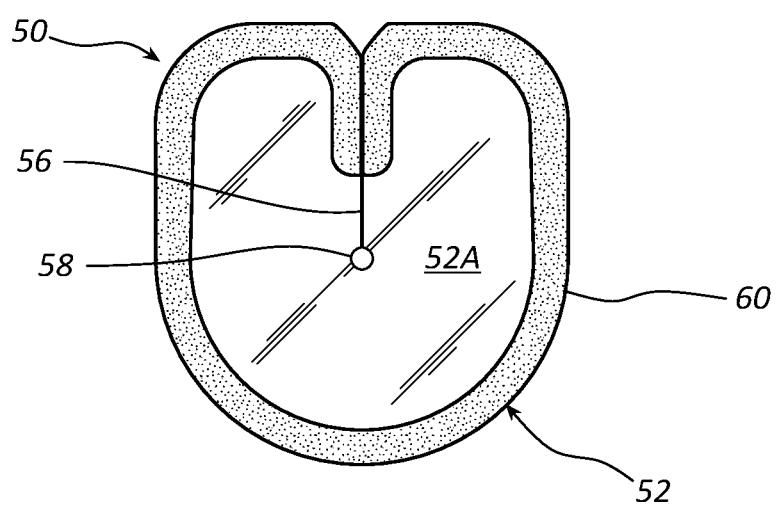
FIG. 11 is a top view of an antimicrobial dressing.
Figure 12:
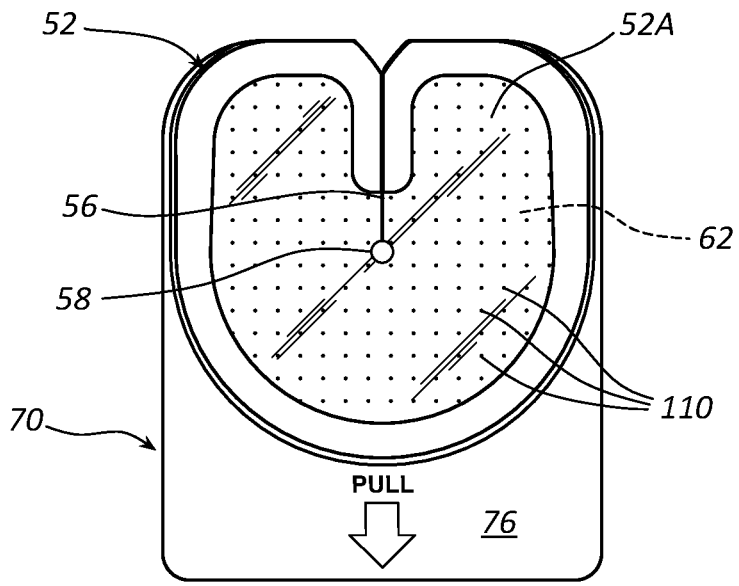
FIG. 12 is a top view of an antimicrobial dressing.

FIG. 10 shows that, in one embodiment, the reinforcement frame 98 can be aligned differently with respect to the release liner 70 and its corresponding pull-tab portion 76. FIG. 11 shows that the reinforcement ring 60 can be composed of various materials, including paper, thermoplastics, rubber, thermoset materials such as silicone, etc. FIG. 12 shows that, in one embodiment, the body 52 of the dressing 50 can include a plurality of perforations 110 defined through the body so as to enable moisture to escape from the skin surface when the dressing 50 is deployed thereon. Such release of moisture can assist in distributing the antimicrobial substance disposed on the bottom surface 52B of the body 52, thus enhancing the antimicrobial effect. Note that the body 52 can include various materials, including nonwoven fabric, mesh material, etc., which allow the body to transmit moisture therethrough.

Figure 13A:
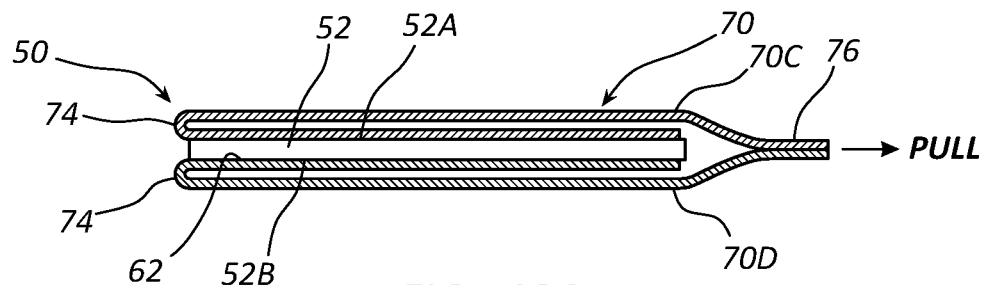
FIGS. 13A and 13B are various views of an antimicrobial dressing.
Figure 13B:
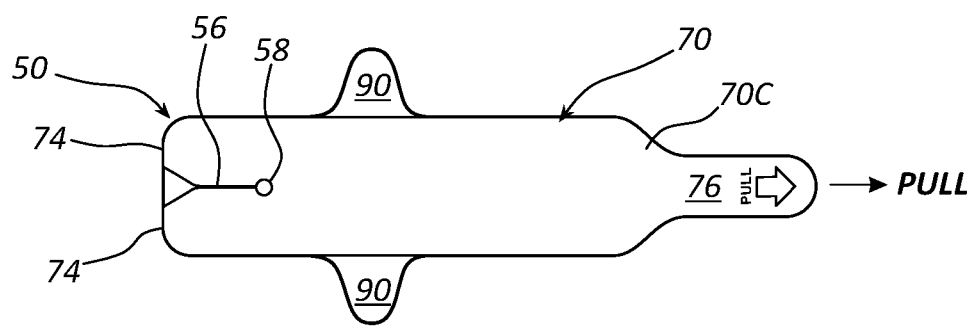

Reference is now made to FIGS. 13A and 13B, which depict various details of the dressing 50 according to another embodiment, wherein the body 52 is interposed between a top release liner 70C and a bottom release liner 70D such that the top surface 52A and the bottom surface 52B of the body are covered thereby. Each of the top and bottom release liners 70C and 70D double back upon themselves at the fold 74, as seen in FIG. 13A, and extend past the body 52 to join together and provide the pull-tab portion 76. The antimicrobial adhesive 62 is disposed on the bottom surface 52B of the body 52, as in previous embodiments. In one embodiment, the antimicrobial adhesive 62 can be disposed on both the top surface 52A and the bottom surface 52B. The slit 56 and central hole 58 are defined through the body 52 and both of the release liners 70C, 70D to enable the dressing 50 to be placed around the catheter 10 or another medical device, as in previous embodiments.

FIG. 13B shows that the dressing body 52 includes the two securement tabs 90 that extend laterally from the body and serve to keep the body 52 in place on the skin surface 22 while the release liners 70C, 70D are removed from the body by a user pulling on the pull-tab portion 76.

In one embodiment, the antimicrobial adhesive can include an absorbent hydrogel, which can assist in migrating the antimicrobial substance about the skin insertion site 20 as it absorbs moisture from the skin of the patient. In another embodiment, the antimicrobial substance can be included on the bottom surface of the body of the dressing without any adhesive.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An antimicrobial full-surround contact dressing for use with a medical device inserted through a skin surface of a patient via a skin insertion site, comprising:
   a flat body consisting of:
      a transparent polyurethane film;
      a reinforcement component of an acrylic material adhered to a top surface of the transparent polyurethane film, the reinforcement component around an outer perimeter of the flat body; and
      an antimicrobial adhesive disposed on a bottom surface of the transparent polyurethane film;
   a slit defined in the flat body configured to enable the flat body to be placed fully around a perimeter of the medical device on the skin surface at the skin insertion site such that a bottom surface of the flat body fully surrounds and contacts the skin insertion site; and
   a release liner removably attached to the bottom surface of the flat body.

2. The antimicrobial full-surround contact dressing as defined in claim 1, wherein the antimicrobial adhesive is a silicone-based adhesive.

3. The antimicrobial full-surround contact dressing as defined in claim 2, wherein the antimicrobial adhesive includes at least one of chlorhexidine gluconate or silver.

4. The antimicrobial full-surround contact dressing as defined in claim 1, wherein the flat body is configured to enable moisture to pass through the flat body.

5. The antimicrobial full-surround contact dressing as defined in claim 4, wherein the flat body includes a plurality of perforations through the flat body to enable the moisture to pass through the flat body.

6. The antimicrobial full-surround contact dressing as defined in claim 1, wherein the release liner includes a folded first release liner and a folded second release liner having folds that meet on the bottom surface of the flat body at a midline of the antimicrobial full-surround contact dressing under the slit.

7. The antimicrobial full-surround contact dressing as defined in claim 1, wherein the antimicrobial full-surround contact dressing includes two securement tabs distributed on opposite sides of the slit as defined by the slit, the two securement tabs configured to enable a user to place two fingers on the two securement tabs, respectively, to maintain the flat body in place when the release liner is removed.

8. The antimicrobial full-surround contact dressing as defined in claim 7, wherein the two securement tabs extend from the reinforcement component, an underside of the two securement tabs including a coated slick surface instead of the antimicrobial adhesive.

9. The antimicrobial full-surround contact dressing as defined in claim 1, wherein a grasp tab is affixed to the release liner, the grasp tab configured to assist a finger of a user to remove the release liner from the flat body.

10. The antimicrobial full-surround contact dressing as defined in claim 1, wherein the transparent polyurethane film is configured to enable an observer to observe the skin insertion site after placement of the antimicrobial full-surround contact dressing on the skin surface of the patient.

11. The antimicrobial full-surround contact dressing as defined in claim 1, wherein the reinforcement component is a ring disposed around the outer perimeter of the flat body.

12. The antimicrobial full-surround contact dressing as defined in claim 11, wherein the reinforcement component is semi-rigid and provide rigidity to the flat body.

13. The antimicrobial full-surround contact dressing as defined in claim 1, wherein the medical device is a catheter.

14. The antimicrobial full-surround contact dressing as defined in claim 1, wherein the flat body is substantially disk-shaped.

15. The antimicrobial full-surround contact dressing as defined in claim 1, wherein the flat body is interposed between first and second release liners, the first and second release liners including pull-tab portions opposite the outer perimeter of the flat body from which the slit extends.

16. A method of dressing a skin insertion site through which a medical device passes into a body of a patient, the method comprising:
   grasping a full-surround contact dressing with a hand of a user, the full-surround contact dressing including:
      a flat body consisting of:
         a transparent polyurethane film;
         a reinforcement component of an acrylic material adhered to a top surface of the transparent polyurethane film, the reinforcement component around an outer perimeter of the body; and
         an antimicrobial adhesive disposed on a bottom surface of the polyurethane film; and
      a slit extending inward from the outer perimeter of the body;
   inserting a portion of the medical device through the slit;
   removing a release liner removably attached to the bottom surface of the body; and
   placing the body fully around a perimeter of the medical device at the skin insertion site so as to fully surround and contact the skin insertion site.

17. The method as defined in claim 16, further comprising securing the body to a skin surface of the patient with a silicone adhesive for the antimicrobial adhesive, the antimicrobial adhesive including at least one of chlorhexidine gluconate or silver.

18. An antimicrobial full-surround contact dressing for use with a medical device inserted through a skin surface of a patient via a skin insertion site, comprising:
   a flat body consisting of:
      a transparent polyurethane film;
      a reinforcement component of an acrylic material adhered to a top surface of the transparent polyurethane film, the reinforcement component around an outer perimeter of the flat body; and a transparent antimicrobial adhesive disposed on a bottom surface of the transparent polyurethane film;

a slit defined in the flat body configured to enable the flat body to be placed fully around a perimeter of the medical device on the skin surface at the skin insertion site such that a bottom surface of the flat body fully surrounds and contacts the skin insertion site, the flat body further configured to enable visual observation of the skin insertion site; and a release liner configured to cover the transparent antimicrobial adhesive until removed by a user when the antimicrobial full-surround contact dressing is placed on the skin surface of the patient.

19. The antimicrobial full-surround contact dressing as defined in claim 18, wherein the flat body is flexible.

20. The antimicrobial full-surround contact dressing as defined in claim 19, wherein the transparent antimicrobial adhesive is a silicone-based adhesive including at least one of chlorhexidine gluconate or silver.

21. The antimicrobial full-surround contact dressing as defined in claim 20, wherein the release liner includes a folded first release liner and a folded second release liner having folds that meet on the bottom surface of the flat body at a midline of the antimicrobial full-surround contact dressing under the slit.

22. The antimicrobial full-surround contact dressing as defined in claim 18, wherein the reinforcement component is a ring disposed around the outer perimeter of the flat body.

\* \* \* \* \*